United States Patent [19]

Ahmad et al.

[11] Patent Number: 5,009,886
[45] Date of Patent: Apr. 23, 1991

[54] DENTIFRICE

[75] Inventors: Mohammad R. Ahmad, Glenview; Oscar A. Barke, Skokie, both of Ill.

[73] Assignee: Floss Products Corporation, Morton Grove, Ill.

[21] Appl. No.: 416,101

[22] Filed: Oct. 2, 1989

[51] Int. Cl.$^5$ .......................... A61K 7/26; A61K 35/78
[52] U.S. Cl. ..................................... 424/58; 424/195.1
[58] Field of Search ............................... 424/58, 195.1

[56] References Cited

U.S. PATENT DOCUMENTS

| 196,275 | 4/1877 | Ward | 424/58 |
| 1,522,410 | 1/1925 | Bluhm et al. | 424/58 |
| 1,527,523 | 2/1925 | Nitardy et al. | 424/58 |

FOREIGN PATENT DOCUMENTS

| 1133831 | 10/1982 | Canada | 424/58 |
| 56-86416 | 7/1981 | Japan | 424/58 |
| 58-55409 | 4/1983 | Japan | 424/58 |
| 58-121218 | 7/1983 | Japan | 424/58 |
| 60-184022 | 9/1985 | Japan | 424/58 |
| 61-122221 | 6/1986 | Japan | 424/58 |
| 988611 | 4/1965 | United Kingdom | 424/58 |

OTHER PUBLICATIONS

Lewis et al. Medical Botany (1977), John Wiley & Sons, N.Y., pp. 244–247, 269–270.

Primary Examiner—Shep K. Rose
Attorney, Agent, or Firm—Charles F. Lind

[57] ABSTRACT

The disclosed dentifrice is comprised of micro-sized particles or microfibers of nondeleterious organic plant components, specifically the branches or roots of trees, botanically known as the azadirachta or *salvadora persica,* and commonly known in different parts of the world as the peelu, miswaak, neem or siwak tree. The dentifrice is otherwise void of any and all mineral abrasives commonly used in dentifrice. The micro-sized particles or microfibers are filtered through and thus are generally sized less than the openings of 20–60 mesh screen; and when moistened by saliva yield a soft nondamaging abrasive for cleaning and whitening the teeth and an astringent for acting on the gums and other soft tissue of the mouth. The micro-sized particles or microfibers may be mechanically ground and then dry filtered through very fine screens, or these micro-sized particles or microfibers may additionally be heated in a bath of deionized water and the composite liquid may then be filtered with only minimal pressure differential through a very fine cloth bag filter of the order of perhaps 20–60 mesh. Additives for taste, healing, color or media consistancy may be blended with the micro-sized particles or microfibers as desired. The dentifrice may be used as a paste, gel, powder, rinse or the like.

2 Claims, No Drawings

DENTIFRICE

BACKGROUND OF THE INVENTION

Tooth decay results from the chemical reaction between oral bacteria and food debris that remains in one's mouth after eating. The bacteria may occur as a film called plaque that forms on the teeth, and can react with the food sugars and starches to produce an acid capable of dissolving tooth enamel. Tartar, a cement-like substance, may form on the teeth, frequently at the gum line or even under the gums, to trap the bacteria-laden plaque against the teeth.

The bacteria also create toxins that can irritate the gums, which can then become diseased or infected. The mildest form of disease is gingivitis, an inflammation of the gums due to the buildup of plaque on the teeth. Periodontitis is a more serious and destructive gum disease, and may progress irreversibly in breaking down the teeth supporting gum and bone tissues. Thus, the gums may detach from the teeth, and if the condition is not treated, the supporting bone may dissolve to the point of the teeth becoming loose, requiring surgical treatment or the removal of teeth.

Moreover, recession of the gums away from the teeth, combined with an increased incidence of gum disease, can expose tooth roots to plaque. As tooth roots are covered with cementum, which is softer than enamel, they are more susceptive to decay and more sensitive to the touch and to hot and cold temperatures.

Effective oral hygiene habits, including brushing and flossing the teeth, are thus imperative if one hopes to keep healthy teeth and gums. As saliva helps to clean one's teeth, stimulation of the buildup of saliva, such as by chewing, may be helpful.

Dentifrice in the form of a paste, gel, powder, rinse or the like, may commonly be used as part of one's personal oral hygiene efforts. In brushing one's teeth with a dentifrice that may include a mineral abrasive, such as calcium carbonate, the abrasive may remove the plaque and/or tarter, whiten the teeth, and make the mouth feel clean However, when used extensively or in excess, the mineral abrasive could actually be too hard, so as to wear and/or even damage the tooth's enamel, that over the years with resulting subsequent erosion could not only allow but be incidental in causing tooth decay.

SUMMARY OF THE INVENTION

The basic object of the present invention is to provide a dentifrice comprised of micro-size fibers of organic nondeleterious plants, such as the branches or roots of specific trees botanically known as the azadirachta or salvadora persica, and commonly known in different parts of the world as the peelu, miswaak, neem or siwak tree. The microfibers combine with the mouth's natural saliva: (1) to yield a nondamaging soft abrasive that may be brushed against the teeth to lift off the plaque and whiten the teeth, and (2) further to yield an astringent that may act beneficially on the gums and other soft tissue of the mouth.

The improved dentifrice may be used in the form of a paste, gel, powder, rinse or the like.

DETAILED DESCRIPTION OF PREFERRED EMBODIMENTS OF THE INVENTION

The specific dentifrice to be disclosed herein utilizes organic nondeleterious plant components, specifically the branches or roots of specific trees, botanically known as the azadirachta or salvadora persica and commonly known in different parts of the world as the peelu, miswaak, neem or siwak tree. The grain structure of this specific tree, in many of its branches and roots, is comprised of many elongated string-like continuous stands located side-by-side and extended longitudinally of the branch or root. Each strand of such branches or roots, which are commonly referred to as sticks, may be of a thickness only several thousandths of an inch (0.001-0.01") across.

For purposes of this disclosure, the sticks referred to will be considered as being from branches or roots of the azadirachta or salvadora persica tree, or the peelu, miswaak, neem or siwak tree; although continued reference will be only to the peelu tree.

This invention utilizes the peelu wood in a specific beneficial manner compared to them in the natural state. The specific dentifrice to be disclosed herein utilizes the wood, and specifically that containing the string-like continuous stands, after it has first been mechanically ground and/or chopped to micro-sized particles. In one mode of use, the mechanically ground and/or chopped particles of the peelu wood are filtered dry through very fine screens, of the order of 20-60 mesh, to yield micro-sized particles, or microfibers. In an alternative mode of use, the mechanically ground and/or chopped particles of the peelu wood are further filtered with a deionized water carrier with only minimal pressure differential, through a very fine cloth bag filter, of the order of perhaps 20-60 mesh, to yield micro-sized particles, or microfibers, suspended in a liquid bath.

When in either the powder mode or in wet modes, the micro-sized particles or microfibers of the peelu wood are perhaps no larger than approximately 0.0001-0.001 inch across. In the inventive dentifrices to be disclosed, these microfibers will be used instead of and will replace any and/or all mineral abrasives, such as calcium carbonate or hydrated silica, commonly used in dentifrice; and provide a soft nondamaging organic abrasive particularly effective for cleansing plaque off of the teeth. Moreover, these microfibers combine with moisture including natural saliva to provide an astringent for the gums and other soft tissue of the mouth.

EXAMPLE 1

One preferred form of specific dentifrice may be a powder, that would be used when brushing one's teeth in an otherwise conventional manner.

To form the powder, the peelu wood is mechanically ground and/or chopped to yield very fine particles, which are dry filtered through very fine screens, of the order of 20-60 mesh, to yield only micro-sized particles or microfibers. Additives, including: an artificial sugarless sweetener such as sorbitol; a flavor enhancer such as mint; a vitamin supplement, such as vitamin C; and a solvent such as vegetable glycerine may be added to the micro-sized particles.

Preferred specific ranges and one specific formulation by weight may be as follows:
  70-90% or 83% 40 mesh filtered fibers;
  3-8% or 1% sorbitol;
  1-2% or 1% mint flavoring;
  1-2% or 1% vitamin C; and
  8-15% or 10% liquid vegetable glycerine solvent.

The components are mixed together and dried in moderate dry 60-90 degrees Centigrade heat for 20-40 minutes, and mechanically mixed again. The finished product is a very fine dry powder and should be packaged in a manner to allow easy discharge in controlled minute quantities, while keeping the product dry before use.

EXAMPLE 2

Another preferred form of specific dentifrice may be a gel, that would be used when brushing one's teeth in an otherwise conventional manner.

To form the gel, a liquid extract is made from the mechanically ground and/or chopped particles of the peelu wood, and then mixed with the needed gelling, healing and flavor additives, etc.

Thus, the mechanically ground and dry filtered peelu wood particles, smaller than the openings of the 20-60 mesh filter used, are heated in a bath of deionized water and a preservative such as methylparaben, for a short duration, and the liquid is then further filtered with only minimal pressure differential through a very fine cloth bag filter to yield the extract liquid having micro-sized particles or microfibers of the peelu wood suspended therein. Preferred specific ranges and one specific formulation by weight to form the liquid extract may be as follows:

75-95% or 88% deionized water;
5-25% or 12% 40 mesh filtered fibers;
0.1-0.5% or 0.25% methylparaben.

The components are mixed together and heated to 70-95 degrees Centigrade for 10-40 minutes; whereupon the liquid is further filtered with only minimal pressure differential through a cloth bag filter, of the order of perhaps 20-60 mesh, to yield the extract liquid.

The additives for making the gel may include an artificial sugarless sweetener such as sorbitol; a flavor enhancer such as mint; a gelling thickener such as carrageenan; a vitamin supplement, such as vitamin C; and a gum healer such as allantoin. Preferred specific ranges and one specific formulation by weight to form the gel may be as follows:

10-20% or 16% deionized water;
30-60% or 50% sorbitol;
15-30% or 20% peelu wood extract liquid;
5-15% or 9% liquid vegetable glycerine solvent.
1-3% or 1% carrageenan;
0.1-2.0% or 1% titanium dioxide coloring;
0.1-0, 5% or 0.2% sodium lauryl sulfate surfactant; and
0.5-2% or 0.75% mint flavor.

The components are mixed together and heated to 60-90 degrees Centigrade heat for 20-40 minutes. After this, the finished gel product can be packaged in collapsible tube and/or pressurized container.

EXAMPLE 3

Another preferred form of specific dentifrice may be a rinse, that would be used with or without brushing one's teeth, or in an otherwise conventional manner.

To form the rinse, the peelu wood liquid extract of Example 2 would be mixed with the needed healing and flavor additives, which may include additional deionized water; an artificial sugarless sweetener such as sorbitol; food color such as beta carotene; a flavor enhancer such as mint; a surfactant such as carrageenen; an astringent such as zinc gluconate; healers such as allantoin and aloevera; a vitamin supplement, such as vitamin C; and liquid vegetable glycerine solvent. Preferred specific ranges and one specific formulation by weight may be as follows:

20-30% or 25% deionized water solvent;
0.01-0.05 or 0.02% beta carotene;
20-40% or 25% extract liquid;
30-50% or 35% sorbitol;
1-2% or 0.75% mint flavor;
0.4-1% or 0.7% zinc gluconate;
0.1-0.5% or 0.3% aloevera; -1-2% or 1% vitamin C;
1-3% or 1% carrageenan;
0.1-1.0% or 0.4% allantoin.

The components are mixed together and heated to 60-90 degrees Centigrade heat for 20-40 minutes, and mixed again. The liquid product will have the micro-sized fiber particles or microfibers held in colloidal suspension. The finished liquid product is reasonably attractive for a rinse and can be packaged in transparent container even.

It has been observed that use of the finer micro-sized particles or microfibers in the dentifrice is preferred, in that they can work to areas on or between the teeth that larger particles cannot reach. Moreover, their greater overall exposed surfaces provides faster and more thorough release when exposed to moisture, including natural saliva, of its astringent chemicals for providing a healing effect on the gums and other soft tissue of the mouth. In all cases, the micro-sized particles or microfibers, of less that approximately 20-60 mesh sizes, provide a soft nondamaging abrasive that when brushed on the teeth provides for cleansing and whitening them, without being sufficiently hard to injure them.

It will be appreciated that other additives may be included in the dentifrice, such as different vitamin supplements including vitamin A (helpful for sustained formation of the tooth enamel), and/or vitamin D and/or phosphorus and/or calcium (each helpful for maintaining tooth and gum strength). Also, fluoride can be added. These components have not been included in the formulations of the Examples given, as they would not change the inventive aspect of the claimed disclosure.

While only specific embodiments of the invention have been disclosed, it is apparent that variations may be made therefrom without departing from the inventive concept. Accordingly, the invention is to be limited only by the scope of the following claims.

What is claimed as our invention is:

1. In a gel dentifrice for caring for one's teeth and gums, the combination of 20-60 mesh or less natural form micro-sized particles or microfibers of the branches or roots of trees botanically known as the azadirachta or salvadora persica, the micro-sized particles or microfibers being formed by mechanically grinding and/or chopping the branches or roots of the trees to very fine particles, dry-filtering these particles through very fine screens, of the order of 20-60 mesh, to yield 20-60 mesh or less micro-sized particles or microfibers, the improvement consisting of the steps of mixing the yielded micro-sized particles or microfibers in a bath of deionized water and a minute quantity of methylparaben and heating the composite liquid to 70-95 degrees Centigrade for 10-40 minutes, and filtering the composite liquid with only minimal pressure differential through a very fine cloth bag filter of the order of 20-60 mesh to yield a filtered liquid having 20-60 mesh or less micro-sized particles or microfibers suspended therein; mixing artificial sugarless sweetener, a flavor enhancer, a vitamin supplement, a gum healer, and a gelling thickener, with the filtered liquid having the micro-sized particles or microfibers suspended therein, thereby providing in the gel dentifrice a natural astringent for acting on the gums and other soft tissue of the mouth and a soft nondamaging abrasive for cleaning and whitening the teeth and otherwise being void of any and all mineral abrasives commonly used in dentifrice; and the gel dentifrice by weight being comprised of 10-20% deionized water; 30-60% sorbitol; 5-15% extract liquid; 5-15% liquid vegetable glycerine solvent; 1-3% carrageenan; 0.1-2.0% titanium dioxide coloring; 0.1-0.5% sodium lauryl sulfate surfactant; and 0.5-2% mint flavor.

2. In a liquid rinse dentifrice for use in caring for one's teeth and gums, the combination of 20-60 mesh or less natural form micro-sized particles or microfibers of the branches or roots of trees botanically known as the azadirachta or salvadora persica, the micro-sized particles or microfibers being formed by mechanically grinding and/or chopping the branches or roots of the trees to very fine particles, dry-filtering these particles through very fine screens, of the order of 20-60 mesh, to yield 20-60 mesh or less micro-sized particles or microfibers, the improvement consisting of the steps of mixing the yielded micro-sized particles or microfibers in a bath of deionized water and a minute quantity of methylparaben and heating the composite liquid to 70-95 degrees Centigrade for 10-40 minutes, and filtering the composite liquid with only minimal pressure differential through a very fine cloth bag filter of the order of 20-60 mesh to yield a filtered liquid having 20-60 mesh or less micro-sized particles or microfibers suspended therein; adding to such liquid extract additional components of an artificial sugarless sweetener, a flavor enhancer, a vitamin supplement, a gum healer, a surfactant, an astringent, and liquid vegetable glycerine solvent, to form the liquid rinse dentifrice with the micro-sized particles or microfibers suspended therein, thereby providing a natural astringent for acting on the gums and other soft tissue of the mouth and a soft non-damaging abrasive for cleaning and whitening the teeth and otherwise being void of any and all mineral abrasives commonly used in dentifrice; and the liquid rinse dentifrice being comprised by weight of 0.01-0.05% beta carotene; 1-2% mint flavor; 0.4-1% zinc gluconate; 0.1-0.5% aloevera; 1-2% vitamin C; 1-3% carrageenan; and 0.1-1.0% allantoin and the balance of said liquid extract.

* * * * *